US009001968B2

(12) United States Patent
Kugland et al.

(10) Patent No.: US 9,001,968 B2
(45) Date of Patent: Apr. 7, 2015

(54) METHOD FOR CHARACTERIZATION OF A SPHERICALLY BENT CRYSTAL FOR Kα X-RAY IMAGING OF LASER PLASMAS USING A FOCUSING MONOCHROMATOR GEOMETRY

(71) Applicant: Lawrence Livermore National Security, LLC, Livermore, CA (US)

(72) Inventors: Nathan Kugland, Los Angeles, CA (US); Tilo Doeppner, Oakland, CA (US); Siegfried Glenzer, Oakland, CA (US); Carmen Constantin, Los Angeles, CA (US); Chris Niemann, Los Angeles, CA (US); Paul Neumayer, Darmstadt (DE)

(73) Assignees: Lawrence Livermore National Security, LLC, Livermore, CA (US); University of California, Los Angeles, CA (US); GSI, Darmstadt (DE)

( * ) Notice: Subject to any disclaimer, the term of this patent is extended or adjusted under 35 U.S.C. 154(b) by 286 days.

(21) Appl. No.: 13/662,038

(22) Filed: Oct. 26, 2012

(65) Prior Publication Data
US 2013/0108022 A1 May 2, 2013

Related U.S. Application Data

(60) Provisional application No. 61/552,285, filed on Oct. 27, 2011.

(51) Int. Cl.
G21K 1/06 (2006.01)
G01N 23/207 (2006.01)
G21B 1/23 (2006.01)

(52) U.S. Cl.
CPC .............. *G21K 1/06* (2013.01); *G01N 23/2076* (2013.01); *G21B 1/23* (2013.01); *G01N 2223/331* (2013.01); *G21K 2201/062* (2013.01); *G21K 2201/064* (2013.01)

(58) Field of Classification Search
CPC ................... G01N 2223/331; G01N 23/2076; G21B 1/23; G21K 2201/062; G21K 2201/064
USPC ........................................................ 378/82–85
See application file for complete search history.

(56) References Cited

U.S. PATENT DOCUMENTS 6,038,285 A * 3/2000 Zhong et al. .................... 378/84
6,259,763 B1 * 7/2001 Bitter et al. ..................... 378/82

* cited by examiner

*Primary Examiner* — Hoon Song
*Assistant Examiner* — Danielle Fox
(74) *Attorney, Agent, or Firm* — Kilpatrick Townsend & Stockton

(57) ABSTRACT

A method is provided for characterizing spectrometric properties (e.g., peak reflectivity, reflection curve width, and Bragg angle offset) of the Kα emission line reflected narrowly off angle of the direct reflection of a bent crystal and in particular of a spherically bent quartz 200 crystal by analyzing the off-angle x-ray emission from a stronger emission line reflected at angles far from normal incidence. The bent quartz crystal can therefore accurately image argon Kα x-rays at near-normal incidence (Bragg angle of approximately 81 degrees). The method is useful for in-situ calibration of instruments employing the crystal as a grating by first operating the crystal as a high throughput focusing monochromator on the Rowland circle at angles far from normal incidence (Bragg angle approximately 68 degrees) to make a reflection curve with the He-like x-rays such as the He-α emission line observed from a laser-excited plasma.

12 Claims, 5 Drawing Sheets

METHOD FOR CHARACTERIZATION OF A SPHERICALLY BENT CRYSTAL FOR Kα X-RAY IMAGING OF LASER PLASMAS USING A FOCUSING MONOCHROMATOR GEOMETRY

CROSS-REFERENCES TO RELATED APPLICATIONS

This application claims benefit under 35 USC §119(e) to U.S. Provisional Application No. 61/552,285 filed on Oct. 27, 2011, the disclosure of which is incorporated by reference herein in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND

This invention relates to imaging x-ray emission spectroscopy and more particularly to the accurate characterization or calibration methods applied to bent crystals, such as quartz crystals, that are used as a part of an in-situ x-ray imaging diagnostic system, such as in a fusion reactor that produces an x-ray emitting plasma.

Spherically and toroidally bent crystals are used as gratings for measuring narrow-bandwidth, two dimensional x-ray images. These crystals are often used for imaging laser plasma x-ray emission with high resolution. The brightness and spectral bandwidth of the resulting x-ray images are fundamentally determined by the wavelength dependent instrument function of the crystal. Additional limits on brightness, spectral bandwidth, field of view and spatial resolution are introduced by the set-up geometry. When imaging narrow-bandwidth x-ray lines, spherically and toroidally bent crystals may provide higher spectral and spatial resolution than other x-ray imaging instruments, such as pinhole cameras or metal-mirror Kirkpatrick-Baez microscopes. Quantitative x-ray imaging involves characterization of the crystal spectrometric properties and imaging performance so that the instrumentation is properly calibrated. Due to extreme selectivity of the imaging technique, lack of calibration leads to false or even no output results.

Despite the advances made in the field of x-ray imaging of laser-generated plasma, there is a need in the art to provide a more accurate and reliable method for characterizing a quartz crystal used for X-ray imaging of laser-generated plasmas.

SUMMARY

According to the invention, a method is provided for characterizing spectrometric properties (e.g., peak reflectivity, reflection curve width, and Bragg angle offset) of the Kα emission line reflected narrowly off angle of the direct reflection of a bent crystal and in particular of a spherically bent quartz 200 crystal by analyzing the off-angle x-ray emission from a stronger emission line reflected at angles far from normal incidence. The bent quartz crystal can therefore accurately image argon Kα (also denoted K-alpha) x-rays at near-normal incidence (Bragg angle of approximately 81 degrees).

The method is useful for in-situ calibration of instruments employing any suitable bent crystal as a grating by first operating the crystal as a high throughput focusing monochromator on the Rowland circle at angles far from normal incidence (Bragg angle approximately 68 degrees) to make a reflection curve with the He-like x-rays such as the He-α (also denoted He-alpha) emission spectrum or "line" observed from a laser-generated plasma.

A specific method for characterizing spectrometric properties of bent crystals comprises selecting a bent crystal, such as a quartz crystal, that is suitable to image selected emission lines of a target substance, positioning the bent crystal on the Rowland circle in the path of x-ray emissions from the target substance also located on the Rowland circle wherein a reflective surface of the bent crystal is disposed at approximately the Bragg angle to the path, repeating iteratively steps to build a rocking curve of x-ray reflections off-angle to the direct reflection angle, namely, exciting the target substance sufficient to generate x-ray emissions to impinge upon the bent crystal, thereupon capturing and recording intensity of a first preselected known narrow spectrum of the x-ray emissions as diverted by the bent crystal at an off-angle to x-ray emission reflections, and incrementally rotating the bent crystal about the center of rotation of its reflective surface, then using the first preselected known narrow spectrum, such as the He-alpha spectrum, to make a rocking curve at angles far from normal incidence, namely at Bragg angles near 70 degrees, that characterizes the crystal at a second preselected known narrow spectrum of a lower energy level, and characterized by a larger Bragg angle, for use as an imaging optic at the second preselected known narrow spectrum, namely the K-alpha spectrum, at angles close to normal incidence wherein the Bragg angles are 80 to 89 degrees.

The exciting step is produced by laser irradiation of a supersonic argon gas jet and the x-ray emissions are from plasma produced by the laser irradiation. Preferably the bent crystal is disposed on a rotatable mount. The selected bent crystal is usable for off-angle imaging at near a 90-degree angle of reflection. The bent crystal is preferably spherically bent at a radius of curvature of equal to twice the radius of the Rowland circle. This configuration is known in the art as the Johann geometry.

In the specific applications contemplated the first preselected known narrow spectrum is of the He-α emission line and the second preselected known narrow spectrum is of the Kα emission line.

Numerous benefits may be achieved by using the techniques described herein. In some embodiments, by enabling in-situ characterization of the crystal used in the Laser Inertial Fusion Engine results in a smaller effective alignment error when the crystal is used for imaging. This enables better alignment of high energy, single-shot lasers used in a fusion reaction where successful laser-plasma imaging is desired. In addition, the techniques described herein can be used for characterizing the crystals that are used for imaging rare-gas x-ray lines.

These and other embodiments of the invention along with many of its advantages and features are described in more detail in conjunction with the text below and attached figures.

DETAILED DESCRIPTION

The brightest x-ray lines from most mid-Z laser plasmas are radiated from the He-α and Kα atomic transitions. Study of this x-ray line self-emission provides insight into the target physics, since the emission is determined by the population level kinetics of the plasma. Correspondingly, multi-wavelength imaging of a plasma can identify gradients in ionization state and temperature. When the crystal spectrometric properties are known, it becomes possible to determine the number of emitted photons from the detector exposure and thereby infer absolute ion populations within the plasma. Additionally, x-ray imaging of Kα fluorescence can be used to trace the transport of energetic laser-accelerated electrons within dense plasmas.

Laser plasmas that emit He-α and Kα also serve as very bright, short duration (e.g., as few as between 10 and 100 picoseconds) x-ray sources for dense plasma diagnostics. Two such diagnostics are x-ray scattering, which can determine fundamental plasma properties and particle correlations, and radiography, which can measure the hydrodynamic evolution of dense matter, including phenomena such as such as shock coalescence, compression, and implosion dynamics. Spherically and toroidally bent crystals can be used for x-ray imaging in both scattering and radiography applications. In some embodiments, a measurement of the peak reflectivity, reflection curve width and the Bragg angle offset of a spherically bent quartz crystal intended for quantitative imaging of Ar Kα at 2957 eV and $\theta_B$~81°, by making a calibrated reflection curve using Ar He-α resonance line x-rays at 3140 eV and $\theta_B$~68°, is provided.

Figure 1:
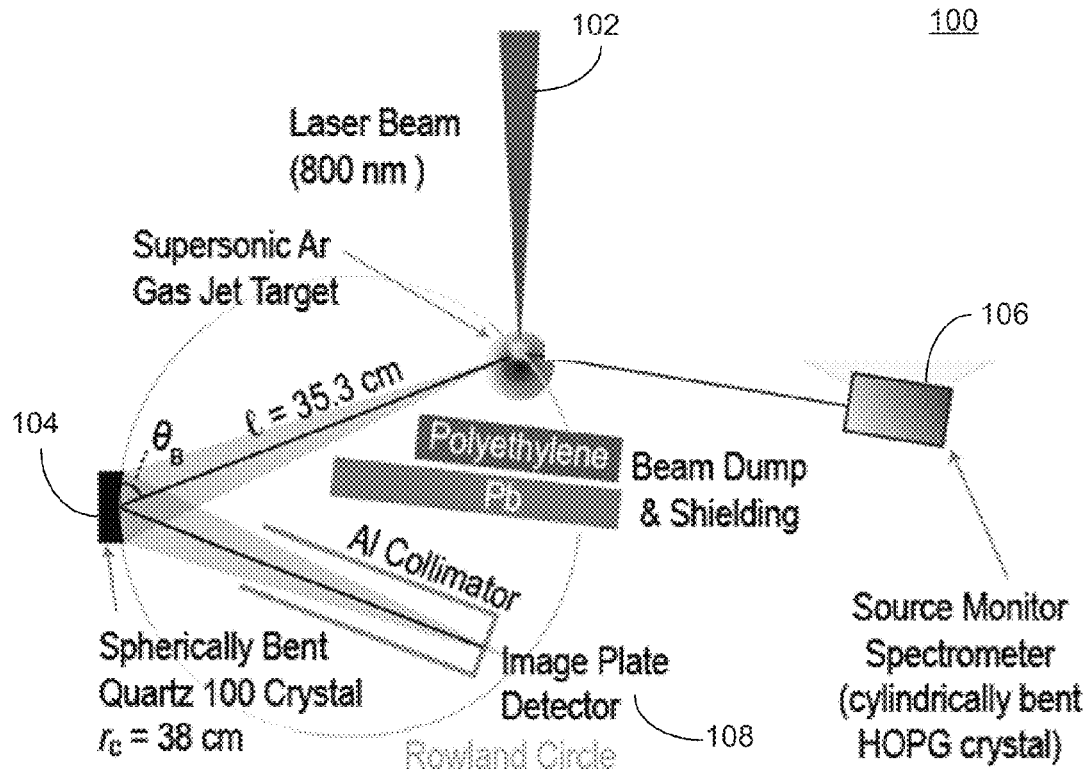
FIG. 1 is a top plan view of a configuration used for practicing the method according to the invention.

FIG. 1 illustrates a configuration of a system 100 for calibrating and measuring the peak reflectivity according to an embodiment of the present invention. System 100 uses a laser source 102, a spherically bent quartz crystal 104, a diagnostic device 106, and an image plate detector 108. Spherically bent quartz crystal 104 is placed on the Rowland circle. In this configuration, the crystal functions as a grating in a high-throughput focusing monochromator. Laser plasma source 102 is used as the x-ray source to obtain an in-situ crystal characterization with no additional equipment. In some embodiments, laser source 102 may be an exciter for stimulating x-ray emission out of an Ar gas jet target. The surface averaged peak reflectivity of spherically bent quartz crystal 104 was 0.25±35% with a reflection width of 0.12 degrees and a Bragg angle offset of +0.27±0.12 degrees. The brightness of the He-α resonance line, as well as its spectral stability over a range of plasma temperatures makes it well-suited for use as an x-ray source for crystal calibration. Crystals intended for imaging Kα x-rays at near normal incidence have appropriate 2d spacings for making rocking curves with He-α in the focusing monochromator geometry as shown in Table 1 below.

TABLE 1

| Quartz Cut | 2D (nm) | Order | Element | Kα (eV), $\theta_B$ | He-α$_{res}$ (eV), $\theta_B$ |
|---|---|---|---|---|---|
| 200 | 0.4246 | 1 | Ar | 2957, 80.16° | 3140, 68.11° |
| 20-23 | 0.2749 | 1 | Ti | 4511, 89.37° | 4750, 71.74° |
| 21-31 | 0.3082 | 2 | Cu | 8048, 88.98° | 8392, 73.51° |

The in-situ rocking curve technique described above is particularly helpful for characterizing crystals intended for imaging rare gas K-shell x-rays, since in general these crystals cannot be characterized using a solid-state x-ray source without going to a different diffraction order, which alters the spectral response.

In some embodiments, laser source 102 can be a Ti:Sapphire laser that provides up to 10 J of 800 nm light in pulses as short as 100 femtoseconds, for on-target intensities above $10^{19}$ W/cm$^2$. The x-ray source can be Ar plasma formed by ultra-short pulse laser irradiation of a supersonic Ar gas jet. In some embodiments, diagnostic device 106 can be an x-ray spectrometer that monitors the source x-ray spectrum using highly oriented pyrolytic graphite (HOPG) crystal that may be cylindrically bent. For moderate photon energies, spherically bent quartz crystals with interplane spacing 2d intended for imaging Kα at Bragg angles $\theta_B$ close to 90° can be characterized by taking a rocking curve of the He-α emission from the same plasma at Bragg angles near 70°. In this instance, the crystal is no longer an x-ray imager but instead functions as a narrow spectral window, high-throughput monochromator, i.e. the narrow-bandwidth limit of a spectrometer. The Kα photon energies hv specified herein are those that would be observed from neutral, isolated matter. As illustrated in Table 1 above, 200 in first order is synonymous with 100 in second order.

Figure 2:
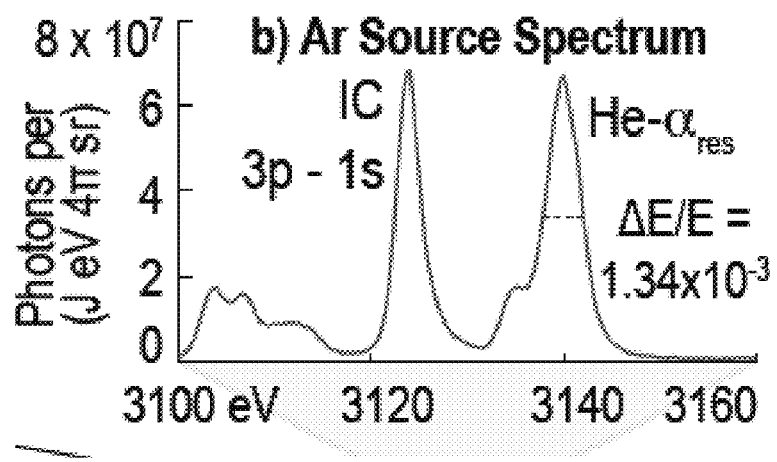
FIG. 2 is a graph illustrating the spectrum of an argon source as detected by the source monitor in FIG. 1.

FIG. 2 illustrates an x-ray spectrum of the Ar gas jet emission that is taken using a source monitor spectrometer (e.g., diagnostic device 106 of FIG. 1 in the form of an HOPG crystal) according to an embodiment of the present invention. As illustrated in FIG. 2, spectrum of the source is shown, as used in the von Hamos geometry. As can be seen, the spectrum for the 3p-1s transition is centered at around 3.12 keV, (i.e. in the middle of the Ar K-shell spectrum), where the Bragg angle was about 36.3° and the source to crystal distance/was about 171 mm±5%. The HOPG crystal had interplane spacing 2d=0:67 nm, a mosaic spread of 0.8°, a width w=25.4 mm+5% and an integrated reflectivity $R_{int}$=3.0 mrad±10%. The x-rays selected by the bent crystal 104 were detected on an absolutely calibrated Fujifilm imaging plate 108. Filtering consisted of 25 μm of Be to block visible light and 84 μm of mylar to attenuate the x-rays, yielding a transmission of $\tau_F$(hv=3.14 keV)=0.24+5%. The measured line width of He-α as shown in FIG. 2 consists of the natural line width $\Delta E/E$=3×10$^{-4}$ as well as contributions, in order of descending importance, from the 230 μm source size of the emitting plasma, thermal Doppler broadening, effects inherent to the crystal and the 25 μm$^2$ pixel size of the image plate. Summing instrumental contributions in quadrature, it was estimated that there was a minimum instrument function width of 2.9 eV at 3.14 keV for a spectrometer resolution $\Delta E/E$=9.6×10$^{-4}$. This places an upper limit of $\Delta E$ at about 3.0 eV on the source function width.

The He-α x-ray source brightness can be obtained by a photometric analysis of the HOPG spectra. Source monitor spectrometer throughput is given by the following equation.

$$\eta_{sms} = \tau_F \frac{R_{int} \frac{w}{l}}{4\pi} \quad (1)$$

where $\tau_F$ is the filter transmission, $R_{int}$ is the integrated reflectivity, w is the crystal width, and l is the source to crystal distance. In a particular embodiment, $\eta_{sms}$=8.4×10−6+12%, where the propagated uncertainty may be estimated assuming no cross correlations. The detector exposure, in units of photo-stimulated luminescence (PSL)57, is then given by $N=N_0 \eta_{sms} C_{IP}$, where $N_0$ is the number of photons emitted from the source into 4π and $C_{IP}$(hv=3 keV)=0:002±10% PSL/(3 keV photon) is the image plate calibration factor. Using our measurement of N, we calculated that for the resonance line $N_0$=2.1×10$^{11}$ photons into 4π per joule of laser energy, for a laser to He-α$_{res}$ conversion efficiency of 1.0×10$^{-4}$±35%. This total uncertainty may include a ±32% random uncertainty from shot-to-shot variations in the short pulse laser pulse conditions.

Figure 3:
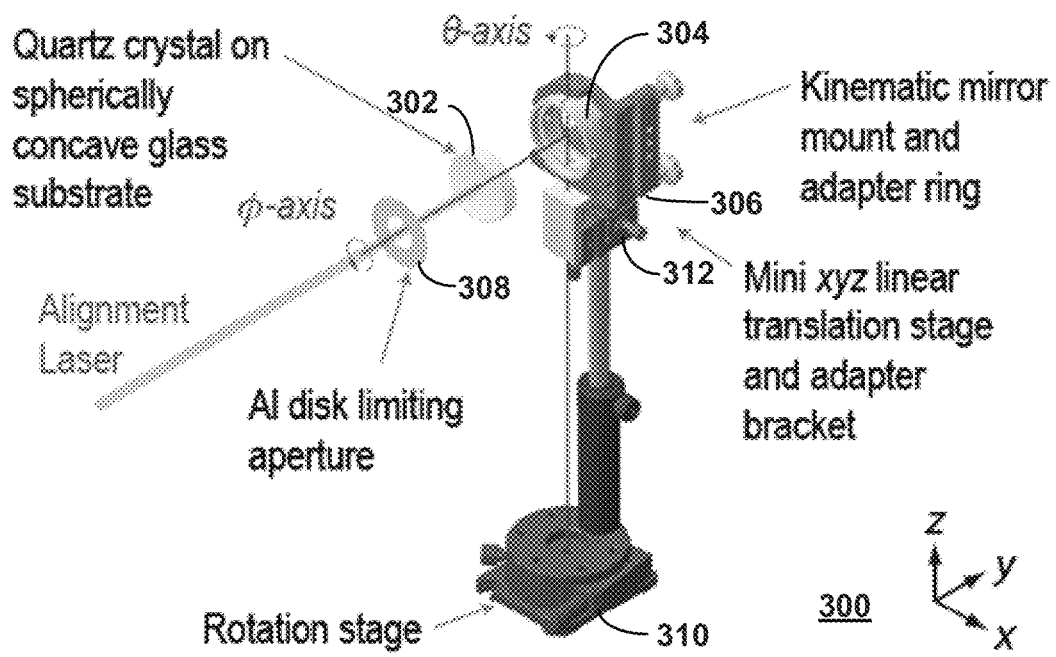
FIG. 3 is a perspective exploded view of a bent crystal with a rotatable mount.

FIG. 3 illustrates a mounting assembly 300 for a spherically bent crystal according to an embodiment of the present invention. A spherically bent quartz crystal 302 having radius of curvature, $r_e$, of about 38 cm may be held inside an adapter ring 304 within a standard kinematic mirror mount 306. An aperture of radius, $r_a$, of about 1.4 cm, which limits the crystal solid angle, is cut into a Al disk 308 which about 500 mm thick (thick enough to be opaque to 3 keV photons). Disk 308 is mounted about 1 mm in front of crystal 302 on a ledge built into adapter ring 304. A manual rotation stage 310 may be used to set the Bragg angle $\theta_B$ with an accuracy of ±2.5 arc minutes. A miniature xyz dovetail linear translation stage 312 directly underneath mirror mount 306 allows for stable linear adjustment with a minimal lever arm. Rotation of crystal 302 about its surface normal, i.e. the φ-axis, may be done by rotating adapter ring 304 manually within mirror mount 306.

Crystal alignment may be performed in two steps: (1) centering the optical assembly, i.e. placing the crystal surface at the intersection of the θ and φ axes, and (2) placing crystal 302 in the chamber and alignment of the Bragg angle $\theta_B$ with respect to the laser plasma x-ray source. Initial alignment may be performed outside of the target chamber, using a flat mirror in place of the crystal and a continuous-wave green (543 nm) HeNe pencil-beam laser with a beam diameter of about 1 mm. An iterative procedure may be used to simultaneously (a) center the reflective surface of the flat mirror on the θ-axis, and (b) move the entire crystal mounting assembly so that the θ-axis intersects the HeNe alignment beam. (The θ axis is the axis of rotation of rotation stage 310 at the base of the crystal mounting apparatus.) The mirror used for initial alignment may be rotated to θ=0°, as measured from the surface of the mirror to the beam axis, and translated so that the beam just grazes the mirror surface. Without moving the mount base, the mirror may be then rotated 180° in θ, to return to grazing incidence but with the mirror now on the opposite side of the beam. Translation in the y-direction at xyz stage 312 combined with adjustment of the mount base may be repeated several times, until the beam is able to just graze the mirror surface at both θ=0° and θ=180°.

Continuing with alignment, the flat mirror is removed and crystal 302 and adapter ring 304 is returned to the mounting hardware. Translating in y brings the center of the crystal surface back to the optical center. Next, while rotating crystal 302 about the φ axis, x and z were adjusted, along with tip and tilt of the kinematic mirror mount, to bring the pole of the spherical surface to be co-linear with the laser axis within the limits of the crystal substrate and assembly concentricity. Remaining misalignment was visible as an offset radius in the retro reflection as it traced a circle about φ but can be largely neglected due to the symmetry of the reflection angles. Next, the crystal mounting assembly is moved into the target chamber and aligned to the plasma x-ray source, placed such that crystal 302 and the plasma x-ray source both fall on the Rowland circle as shown in FIG. 1 and FIG. 2. The HeNe alignment laser sighted through the location of the target plasma at the focal point of the main laser beam. Spherically bent quartz crystal 302 was placed at l=35.3 cm±2% away from the target. With the optical retro reflection of the alignment laser off the crystal front surface, the θ-axis was zeroed to an accuracy of half a HeNe spot diameter over about 30 cm, i.e. ±1.7 mrad, and then set the Bragg angle $\theta_B$ to about 67.67°±0.12°, where the propagated error can be estimated assuming no cross correlations. In this instance, crystal 302 can be considered to be a focusing monochromator, e.g., a Johann spectrometer in the limit of very narrow spectral bandwidth.

Figure 4A:
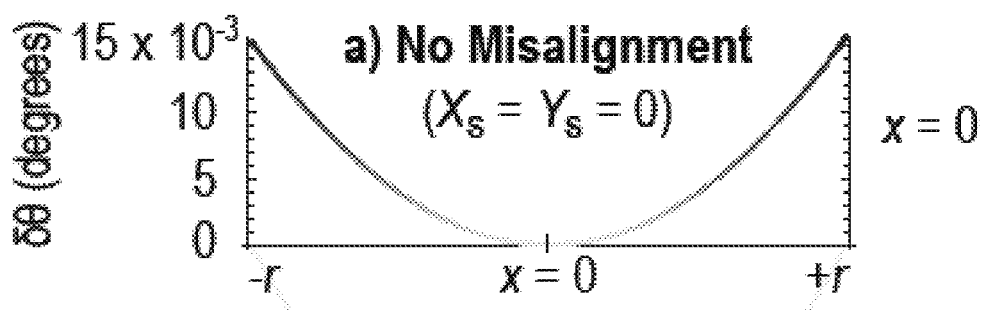
FIG. 4A is a graph illustrating effects of misalignment of the bent crystal of FIG. 4D.
Figure 4B:
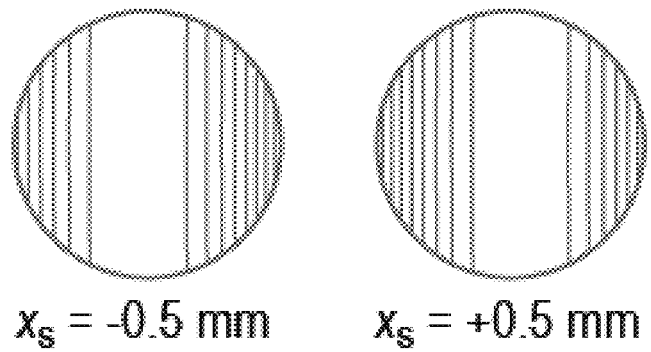
FIG. 4B is an illustration of source misalignment along the x-axis.
Figure 4C:
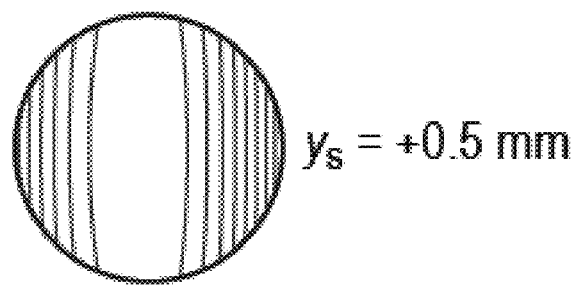
FIG. 4C is an illustration of source misalignment along the y-axis.
Figure 4D:
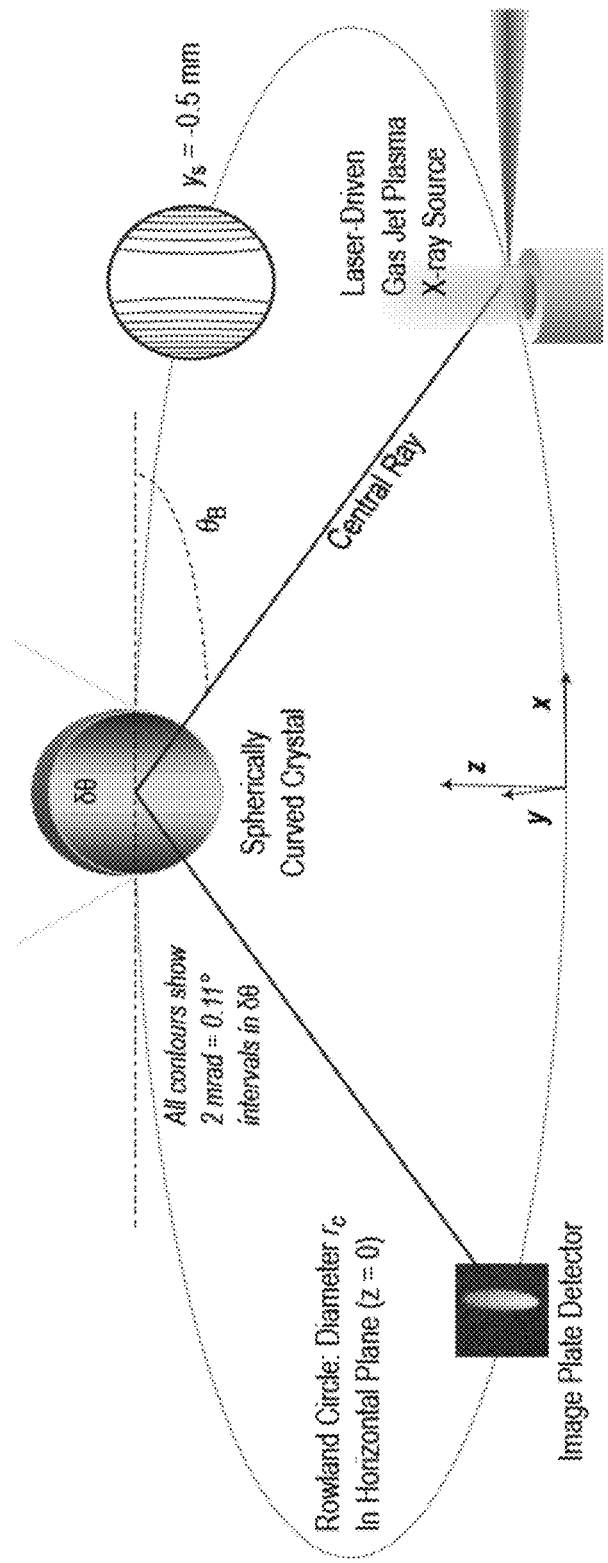
FIG. 4D is a perspective view of a bent crystal grating in a Rowland circle.

The collimator and detector were then aligned using the optical reflection off the crystal surface and placed with the image plate detector (e.g., detector 108 of FIG. 1) at distance of about 32 cm from the crystal. As described below, the x-rays follow a slightly different path than the visible HeNe light because of a bias angle between the crystal lattice and the polished crystal front surface. In a particular embodiment, the detector can be about 50 mm in diameter, which can accommodate a maximum offset of about 37 mrad. The detector must be large enough to ensure that the x-rays do not walk off the sensitive region during the calibration procedure, keeping in mind that the exit angle is $2\theta_B$. The detector may be repositioned as required. Once alignment is complete, the surface of the crystal is protected from target plasma and lightweight debris. In order to accomplish this, the aperture hole can be covered with a layer of 1 μm thick Mylar foil, which is essentially transparent to 3 keV x-rays. Shielding of the detector can be provided by bricks of polyethylene, to stop laser accelerated charged particles without creating energetic x-ray fluorescence, and also using lead, which may also be used due to its opacity to x-rays over a broad range of photon energies. The bricks are placed between the plasma source and the image plate detector. Good shielding and collimation can reduce the noise and background on the image plate detector, especially when studying a rare-gas x-ray line, for which solid foil transmission-edge filters may not be available. FIG. 4A illustrates results from an arrangement of the x-ray source, the crystal and the detector on the Rowland circle. As illustrated in FIG. 4A, without misalignment, the Bragg angle offset δθ varies parabolically across the spherical surface of the crystal. FIGS. 4B and 4C illustrate that misalignments of the x-ray source, the crystal and the detector can cause substantial overall shifts in $\theta_B$ as well as distortions in the δθ profile. FIG. 4D illustrates the relative placement of the x-ray source, the crystal and the detector on the Rowland circle according to an embodiment of the present invention.

Multi-keV x-rays can be imaged using bent crystals as diffracting optics (gratings) in either reflecting Bragg or transmitting Laue geometries, which are suitable for moderate or high photon energies, respectively. In the reflection geometry, photons with wavelength λ reflect from a crystal with inter-plane spacing d according to the Bragg condition $$2d \sin \theta_B = m\lambda \quad (2)$$

where $\theta_B$ is the angle of incidence measured from the surface and m=1;2;3 . . . is the order of reflection. Holding 2d constant, the derivative of this equation yields a convenient relation for the spectral bandwidth given by $$\frac{\Delta E}{E} = \frac{\Delta\theta}{\tan\theta_B} \quad (3)$$

where the angular bandwidth $\Delta\theta$ is specified in radians. Spherically bent crystals used for x-ray imaging are preferentially used near normal incidence (e.g., $\theta_B\sim 90°$) for the highest spatial resolution mainly to minimize off-axis geometric distortions and aberrations, and to achieve nearly monochromatic reflection, as is described below. Reflected signals can be considered as the convolution of a photon source function with the spectral and spatial response functions of the optics and the detector. The spectral response of a crystal to x-rays is commonly known as the instrument function, which can be studied by measuring the throughput of a collimated, narrow-bandwidth x-ray line source reflected from the crystal as it is tilted through a small range of Bragg angles. This results in a reflection curve or rocking curve of width $w_c$, with reflectivity described by $$R(\theta; w_c; R_{max}) \quad (4)$$

where R is the fraction of incident radiation reflected by the crystal. The instrument function is sharply peaked, often well approximated as a Lorentzian, and centered on the Bragg angle, i.e. $R_{max}=R(\theta=\theta_B)$. Equivalently, the entire reflection curve may be obtained at once if the source is fully divergent, the crystal spectral bandwidth exceeds the source spectral bandwidth and the detector is large enough. During the manufacture of bent crystals, lattice distortion may be introduced in proportion to the amount of bending. Furthermore, inaccurate polishing of the crystal flats before bending can introduce a bias angle, i.e. a misalignment of the crystal planes relative to the front surface. This can be measured in bent quartz to be up to 0.23 degrees=4 mrad (i.e. 2 mm offset measured at a distance of 2×250 mm), which means that the rocking curve can vary considerably from crystal to crystal. Specifically, the peak of the reflection curve may be shifted away from the nominal Bragg angle. Any such offset must be considered when aligning the crystal for a specific x-ray line, e.g. through the use of an "effective" 2d spacing to compensate for the offset.

The number of x-ray photons N reflected by a crystal can be calculated by convolving the source photon spectrum, J, with the crystal reflection curve R (Eq. 4) over the area of the crystal. J can be obtained by de-convolving a measured source spectrum from the spectrometer instrument function. In an embodiment, J can be obtained from an x-ray spectrum simulated with the FLYCHK code and then calibrated against the measured source spectrum from FIG. 2. Plasma simulation parameters used as FLYCHK inputs are known in the art. For spherically bent crystals operated with unit magnification as described above and a circular aperture, the crystal area $A=\pi r_a^2$ and the number of reflected photons N is given by the integral $$N = \frac{A\sin\theta_B}{4\pi l^2} \int\int J(\lambda, 2d) * R(\theta, w_c, R_{max}) dX dZ \quad (5)$$

$$\theta = \theta_B + \delta\theta \quad (6)$$

where $\theta$ is the crystal surface angle found at the point on the crystal given by the dimensionless, normalized Cartesian coordinates $X=x/(2r_c); Z=z/(2r_c)$. Although the central ray is aligned to the nominal Bragg angle $\theta_B$, the surface angle varies according to the offset given by $$\delta\theta(X, Z, \theta_B, r_a, r_c, x_s, y_s, z_s). \quad (7)$$

The variation $\delta\theta$ depends on many factors: the location of a given differentially small reflecting element on the crystal surface, the nominal Bragg angle, the shape of the crystal (via the active area that is proportional to $r_a$ and bending radius $r_c$) and source misalignment $x_s$, $y_s$, and $z_s$. For spherically bent crystals, $\delta\theta$ is generally insensitive to misalignment in z but highly sensitive to misalignments in x and y. For larger values of $\theta_B$ such as those used herein, the variation in Bragg angle for a spherically bent crystal is essentially one dimensional and parabolic along X, with some asymmetric distortion possible due to source misalignment. The behavior of $\delta\theta$ is illustrated in FIGS. 4A-4C.

By using Eq. 2 above to change J(X, 2d) to J($\theta$) we can evaluate Eq. 5 as a double-integral purely in X and Z, so long as we include 2d as a free parameter during data fitting. The total spectral bandwidth (cf. Eq. 3) can be approximated as $$\Delta\theta \sim \max(\delta\theta). \quad (8)$$

For near-normal incidence imaging, i.e. $\theta_B>80$ degrees, $\Delta\theta$ is quite small, on the order of $10^{-4}$ degrees. In this work, farther from normal incidence and with a relatively large aperture, $\delta\theta$ is as large as $10^{-2}$ degrees (e.g., See FIGS. 4A-C) and Eq. 5 must be fully evaluated over the circular aperture where $X^2+Z^2 \leq (r_a/(2r_c))^2$. Even so, the spectral bandwidth $\Delta\theta$ is narrow and at each Bragg angle the crystal may reflect only a small slice of the source spectrum. For example, the He-$\alpha$ resonance line from FIG. 2 is approximately 0.17 degrees wide, which is several orders of magnitude larger than $\Delta\theta$. For a given Bragg angle, the spectral window is smallest if the source and crystal are both set on the Rowland circle.

Figure 5A:
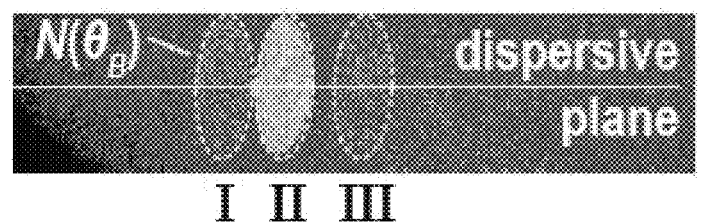
FIG. 5A is a photo image of a monochromatic spectrum used for calibration.
Figure 5B:
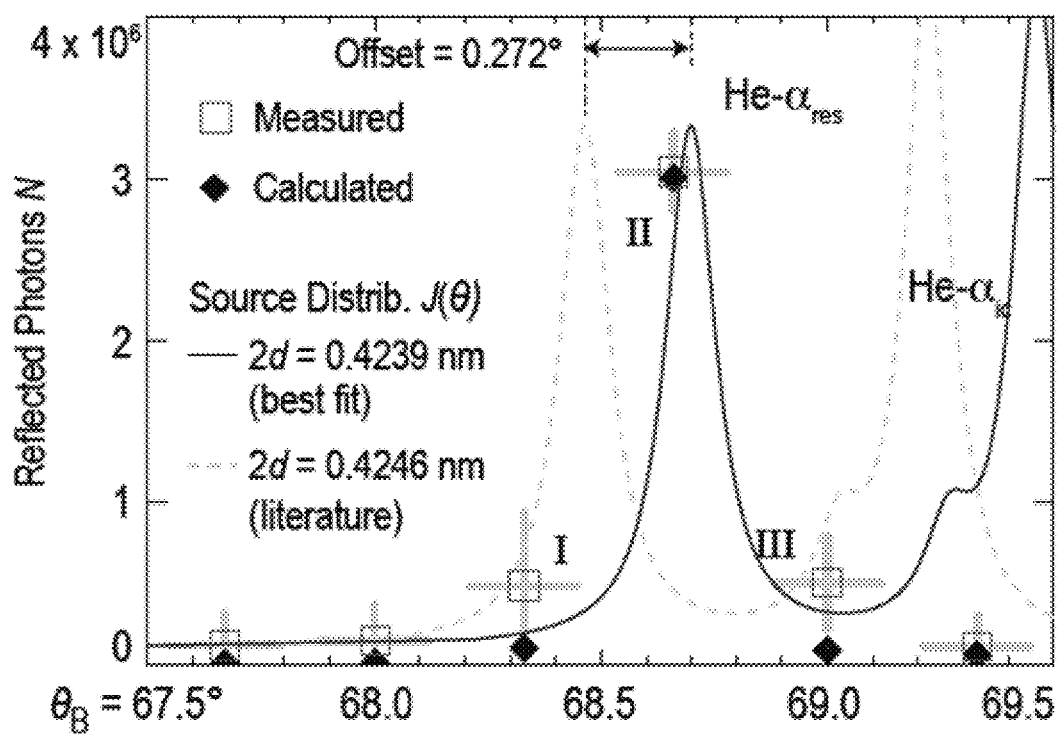
FIG. 5B is a graph showing comparison of calculated and measured spectral values.

FIG. 5A illustrates the image plate exposures taken as part of measurement of crystal parameters according to an embodiment of the present invention used to characterize the specific crystal. FIG. 5B illustrates a calibrated reflection curve of a spherically bent quartz 200 crystal at 3.14 keV according to an embodiment of the present invention in comparison with a calculated reflection cure. The difference is instructive.

Starting at 67.5 degrees, a series of laser shots were taken to build up a reflection curve, advancing the Bragg angle after each shot and always moving in the same direction to avoid backlash in the rotation stage. The photons reflected in first order (m=1) were detected on the image plate (illustrated in FIG. 5A) and were summed to obtain the number of reflected photons N($\theta_B$), as shown in FIG. 5B. Using the calibrated source spectrum with Eq. 5, iterative data fitting found best-fit values for the free parameters in Equations. 5 and 7 above as follows:

$2d=0.4239$ mm $R_{max}=0.25$ $w_c=0.118°$ $x_s=-0.044$ mm $y_s=-0.124$ mm  (9)

It is to be noted that the values described above are based on a specific setup of the bent quartz crystal and other components in the system. One skilled in the art will realize that the values described above will change based on change in other parameters of the equations and setup. The difference between this calculated 2d value and that shown in Table 1 can be a Bragg angle offset due to misalignment of the crystal planes with the polished surface, and may correspond to +0.27 degrees with an uncertainty of ±0.12 degrees, as described above. Compensation for this offset is needed to achieve peak reflectivity when using the crystal for imaging.

The value of the peak reflectivity $R_{max}$, which represents the average over the entire exposed crystal surface, is somewhat higher than what has been measured for spherically bent quartz 100 using solid state x-ray sources and is much higher than the value expected for a quartz 100 flat. Bent crystals are known to have up to 20× higher reflectivity than similar flat crystals due to partial mosaicity from lattice dislocations introduced during bending. This same crystal when later characterized at one spatial point using an x-ray tube source revealed that $R_{max}$=0.11 and $w_c$=0.23°. The lower peak reflectivity and wider rocking curve might be explained by local variation in the crystal quality, as well as by the fact that this offline calibration was done in second order (m=2) with Fe Kα at 6.4 keV instead of in first order at 3 keV.

Ordinate error bars in FIG. 5B indicate the amplitude of noise on the image plate relative to the signal amplitude. There is also a possible systematic uncertainty of ±35% from the calibration of Jusing the source monitor spectrum described above. It should also be noted that the best-fit values for source offsets $x_s$ and $y_s$, mentioned above are not unique. In other words, there exists an extended region in the $x_s$-$y_s$ plane (roughly corresponding to constant angular misalignment) within which fit error is minimized. However, from the practical point of view those parameters inherent to the crystal (e.g., 2d, $R_{max}$, and $w_c$ and not the source misalignment during the characterization that are of concern.

In the case of a typical imaging arrangement for Kα, where $\theta_B$=81 degrees and the aperture radius $r_a$=0.5 cm, the maximum Bragg angle variation $\Delta\theta$ is only on the order of $10^{-3}$ degrees. Therefore, the field of view for the x-ray image is limited primarily by the width $w_c$ of the rocking curve. At a typical working distance of 1~30 cm, the crystal-limited field of view (for a perfectly monochromatic source) is given by 1 $w_c$~620 µm. For a real x-ray source with non-zero line width, the angular field of view can be estimated as the convolved width of the crystal instrument function and the x-ray spectrum.

As described above, operation on the Rowland circle minimizes crystal spectral bandwidth, i.e., it maximizes the crystal area that reflects a small bandwidth. This offers higher detector exposure, but also requires multi-shot operation to obtain a rocking curve and reduces the sensitivity of the resulting rocking curve to the width of the instrument function. Alternately, the crystal may be used with magnification to make a single shot rocking curve. The description above is related to characterizing a spherically bent crystal intended for imaging Kα x-ray emission from a laser plasma using spectrally-stable He-like x-rays from the same laser plasma.

This has the advantage of remaining in the same reflection order for both characterization and operation, which is generally difficult to achieve in the case of rare gas x-ray lines. The resulting rocking curve provides spectrometric properties that for using the crystal for quantitative x-ray imaging. Moreover, the method and system described above helps to determine the Bragg angle offset, knowledge of which is crucial for obtaining the accurate alignment required for monochromatic imaging. Future applications of this technique may use a finer angular resolution to improve accuracy of the rocking curve and the resulting spectrometric parameters.

While a number of specific embodiments were disclosed with specific features, a person of skill in the art will recognize instances where the features of one embodiment can be combined with the features of another embodiment. Also, those skilled in the art will recognize, or be able to ascertain using no more than routine experimentation, many equivalents to the specific embodiments of the inventions described herein. Such equivalents are intended to be encompassed by the following claims.

What is claimed is:

1. A method for characterizing spectrometric properties of bent crystal comprising:
   a) positioning a bent crystal that is suitable to image selected emission spectra and reflect characteristic x-ray emission spectra of a target substance disposed on a Rowland circle in the path of x-ray emissions from the target substance wherein a reflective surface of the bent crystal is disposed at approximately the Bragg angle to the path;
   b) exciting the target substance sufficient to generate x-ray emissions to impinge upon the bent crystal; thereupon
   c) capturing and recording intensity of a first preselected known narrow spectrum of the x-ray emissions as diverted by the bent crystal at an off-angle to direct reflections of x-ray emission;
   d) incrementally rotating the bent crystal about its reflective center of rotation;
   e) repeating steps b), c) and d) to build a rocking curve of x-ray reflections off-angle to the direct reflection angle;
   f) using the first preselected known narrow spectrum to make a rocking curve at angles far from normal incidence that characterizes the crystal at a second preselected known narrow spectrum of a lower energy level, and characterized by a larger Bragg angle, for use as an imaging optic at the second preselected known narrow spectrum at angles close to normal incidence.

2. The method according to claim 1 wherein the exciting step is produced by laser irradiation of a supersonic argon gas jet and the x-ray emissions are from plasma produced by the laser irradiation.

3. The method according to claim 1 wherein the bent crystal is disposed on a rotatable mount.

4. The method according to claim 1 wherein the selected bent crystal is quartz.

5. The method according to claim 1 wherein the bent crystal is spherically bent.

6. The method according to claim 5 wherein the selected crystal is bent at a radius of curvature equal to twice the radius of the Rowland circle in the Johann configuration.

7. The method of claim 1 wherein the first preselected known narrow spectrum is of the He-alpha emission characteristic.

8. The method of claim 7 wherein the second preselected known narrow spectrum is of the K-alpha emission characteristic.

9. A method for characterizing spectrometric properties of bent crystal comprising:
   a) positioning a spherically bent crystal that is suitable to image K-alpha and reflect He-alpha characteristic x-ray emission spectra of a target substance disposed on a rotatable mount on a Rowland circle in the path of x-ray emissions from the target substance wherein a reflective surface of the spherically bent crystal is disposed at approximately the Bragg angle to the path;

b) exciting the target substance sufficient to generate x-ray emissions to impinge upon the spherically bent crystal; thereupon
c) capturing and recording intensity of He-alpha x-ray emissions as diverted by the spherically bent crystal at an off-angle to direct x-ray emission reflections;
d) incrementally rotating the spherically bent crystal about its reflective center of rotation;
e) repeating steps b), c) and d) to build a rocking curve of x-ray reflections off-angle to the direct x-ray emission reflections;
f) using the He-alpha x-ray emission spectrum to make a rocking curve at angles far from normal incidence that characterizes the crystal at the K-alpha x-ray emission spectrum of a lower energy level, and characterized by a larger Bragg angle, for use as an imaging optic at the K-alpha x-ray emission spectrum at angles close to normal incidence wherein the Bragg angles are between approximately 80 degrees and 89 degrees.

10. The method according to claim 9 wherein the bent crystal is quartz.

11. The method according to claim 9 wherein the exciting step is produced by laser irradiation of a supersonic argon gas jet and the x-ray emissions are from plasma produced by the laser irradiation.

12. The method according to claim 9 wherein the spherically bent crystal is bent at a radius of curvature equal to twice the radius of the Rowland circle.

* * * * *